US009835590B1

(12) United States Patent
Piñeiro Fernández et al.

(10) Patent No.: US 9,835,590 B1
(45) Date of Patent: Dec. 5, 2017

(54) DEVICE AND METHOD FOR CHECKING FUEL PELLETS WITH IFBA

(71) Applicant: TECNATOM, S.A., Madrid (ES)

(72) Inventors: Pablo Jesús Piñeiro Fernández, Madrid (ES); Daniel Gómez Fernández, Madrid (ES); Leandro Gonzalo Langa, Madrid (ES); Victor Orlando Barcenilla Marseliano, Madrid (ES)

(73) Assignee: TECNATOM, S.A., Madrid (ES)

( * ) Notice: Subject to any disclaimer, the term of this patent is extended or adjusted under 35 U.S.C. 154(b) by 73 days.

(21) Appl. No.: 15/339,051

(22) Filed: Oct. 31, 2016

(51) Int. Cl.
| | |
|---|---|
| *G21C 3/20* | (2006.01) |
| *G01N 27/82* | (2006.01) |
| *G21C 3/62* | (2006.01) |
| *G21C 17/00* | (2006.01) |
| *G01N 33/22* | (2006.01) |
| *G21C 3/04* | (2006.01) |

(52) U.S. Cl.
CPC ........... *G01N 27/82* (2013.01); *G01N 33/222* (2013.01); *G21C 3/20* (2013.01); *G21C 3/626* (2013.01); *G21C 17/00* (2013.01); *G21C 2003/047* (2013.01)

(58) Field of Classification Search
CPC ...... G21C 3/626; G21C 3/623; Y10S 376/901
See application file for complete search history.

(56) References Cited

U.S. PATENT DOCUMENTS

| | | | | |
|---|---|---|---|---|
| 5,075,075 A | * | 12/1991 | Kapil ................. | G21C 3/18 376/333 |
| 5,147,598 A | * | 9/1992 | Kapil ................. | G21C 3/18 376/414 |
| 5,242,631 A | * | 9/1993 | Iyer ................. | G21C 3/626 264/5 |

\* cited by examiner

*Primary Examiner* — Giovanni Astacio-Oquendo
*Assistant Examiner* — Alvaro Fortich
(74) *Attorney, Agent, or Firm* — Egbert Law Offices, PLLC

(57) ABSTRACT

Device and method for checking fuel rods with IFBA, their zirconium diboride coating. The device includes a variable magnetic field generator and a magnetic field pickup device, arranged in the vicinity of the rod, as well as a control system for comparing both fields in order to measure the electric conductivity of the rod. The method includes the steps of: arranging the rod to be measured between the generator and the pickup device; generation of a variable magnetic field in the generator; picking-up of the magnetic field; comparison between the generated magnetic field and the picked-up one in order to quantify the electric conductivity of the rod; if the electric conductivity differs from a reference value, consider the rod for checking or recycling.

12 Claims, 2 Drawing Sheets

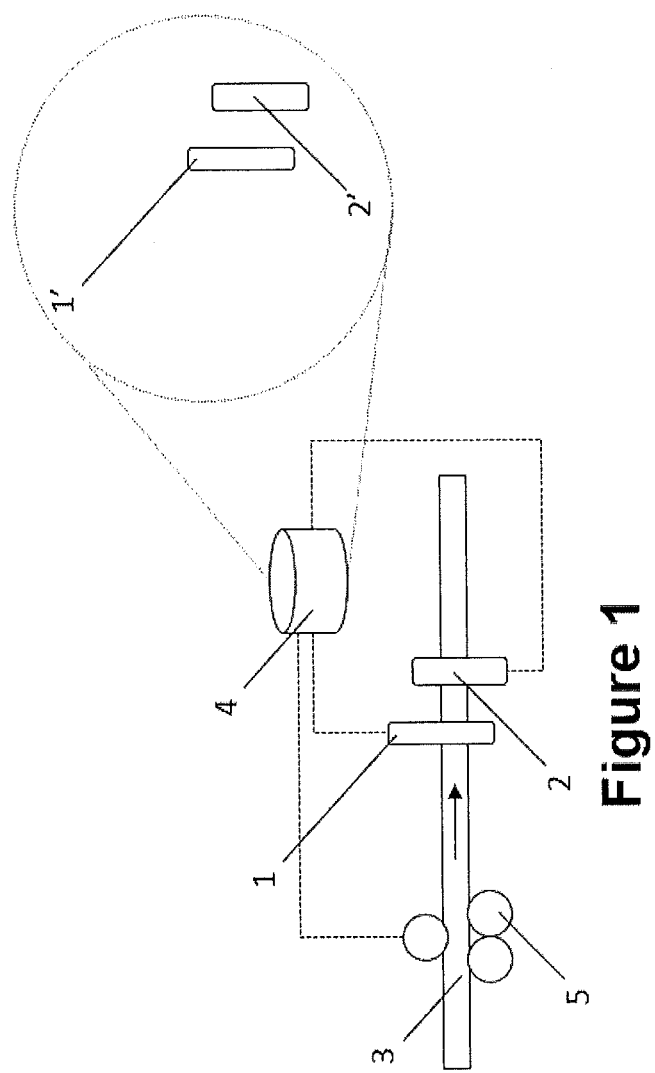

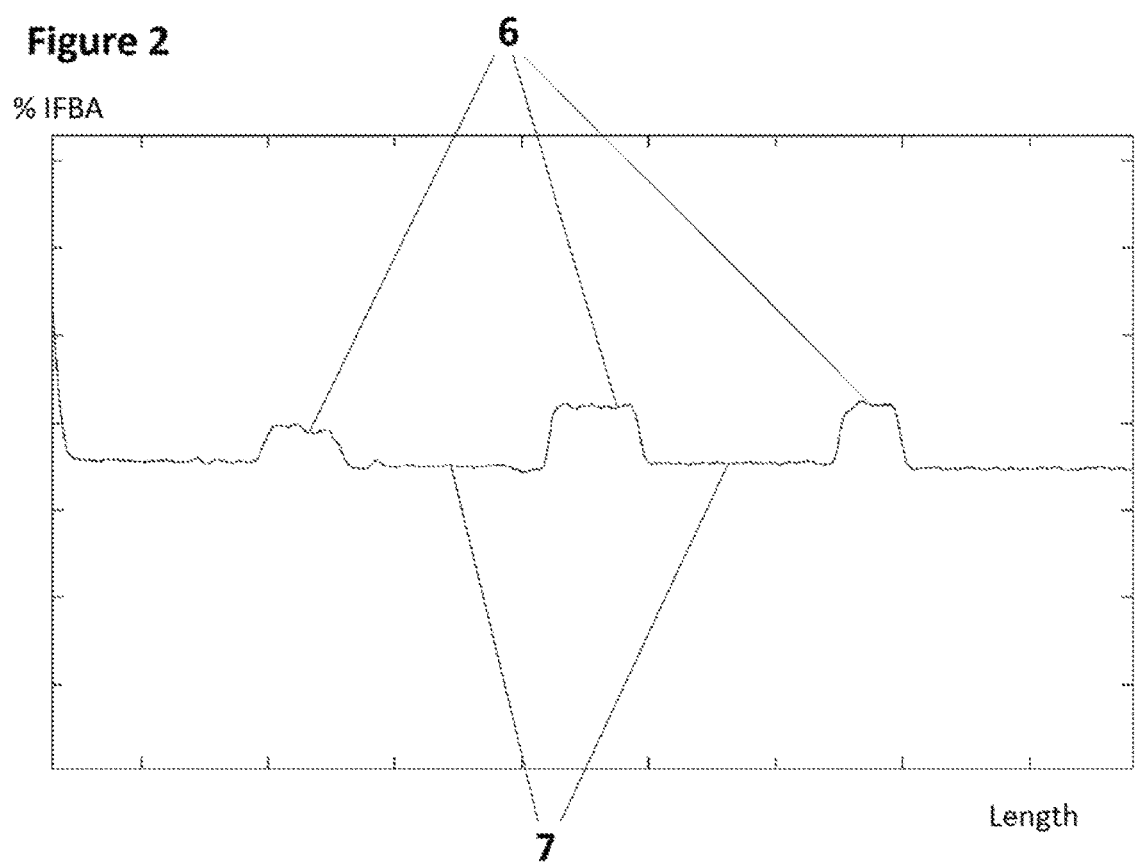

DEVICE AND METHOD FOR CHECKING FUEL PELLETS WITH IFBA

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a device for checking fuel pellets, used for making fuel rods for nuclear power plants, which detects if the position of the pellets with zirconium diboride is appropriate, and if any pellet is diverted. By diverted pellet it is meant that one which is located in an area not deemed for it to be. Either by having a coating in a place where it should be absent or vice versa.

Likewise the present invention relates to the method applied.

2. Description of Related Art Including Information Disclosed Under 37 CFR 1.97 and 37 CFR 1.98

Zirconium diboride $ZrB_2$ is a burnable neutron poison, used in making the fuel rods for pressurized water nuclear reactors. The use of zirconium diboride aims to: satisfy the needs of control of reactivity in new elements, the efficient use of fuel, an extension of the fuel life cycle, the power increase of the reactor and allowing higher burnup degrees.

The fuel pellets with zirconium diboride, consist of fuel pellets of uranium oxide $UO_2$ coated with a film or coating of some microns of $ZrB_2$ (also called IFBA: Integral Fuel Burnable Absorber). The configuration of the fuel rods consists essentially of a zircaloy tube packed with fuel pellets (of about 8 or 10 mm in diameter and about 10 mm in length) and some structural components, varying depending of the product, as a spring, aluminium oxide pellets, supporting tubes, etc. The pellets with IFBA usually take up about 120 inches (about 305 cm) in length and are located in the middle of the rod. At both sides of the IFBA zone, typically there is a length of pellets of about 6 inches (about 15.2 cm) of $UO_2$ having the same enrichment as the pellets with IFBA.

In the fabrication process of these rods it is necessary to control the position of the IFBA zone, the length thereof and the detection of possible diverted pellets, (pellets without IFBA, pellets with a higher thickness of the IFBA layer, etc.).

Currently the IFBA checking is carried in the factory through the combination of two inspections, one in active scanner and the other one in a passive scanner, determining the presence of IFBA by the calculation of the difference in gamma radiation emission obtained in both scanners.

BRIEF SUMMARY OF THE INVENTION

The invention consists of a device and method for checking fuel pellets according to claims. They have the advantage of allowing the determination of presence of IFBA through a single inspection in an active scanner, the inspection being automatable as one more parameter of those currently determined in the analysis of rods in the scanners for checking rods in fuel factories, whether active or passive.

The conductivity degree of $ZrB_2$ as compared to uranium oxide allows perceiving its presence through the variation experienced by an alternating magnetic field in the vicinity of the rod. The detection of this magnetic field variation and its analysis allows knowing the position of the pellets having a $ZrB_2$ coating in the rod, by relating the position of the rod to each reading (at a known steady speed, time and position can be easily related).

Therefore, the device for checking fuel rods (their zirconium diboride coating) comprises a variable magnetic field generator and a magnetic field pickup device, both arranged in the vicinity of the rod to be checked. Likewise, the control system can consist of a second variable magnetic field generator and a second magnetic field pickup device, both identical to the former ones and isolated form the rod to be controlled (for example, remote from the rod). So that the comparison of both magnetic fields allows detecting the variation of the electric conductivity in the rod, as a consequence of the presence or not of the conductive coating thereon.

Preferably, the device further comprises a rod supplier which introduces them at a speed between 10 and 200 mm/s, more preferably 50 mm/s.

In the preferred embodiment, both the generator and the pickup device shall be one or more coils.

The checking method of fuel rods, in turn comprises the steps of:
  Arranging the rod to be measured between the generator and the pickup device.
  Generation of a variable magnetic field in the generator.
  Picking-up of the magnetic field.
  Comparison between the generated magnetic field and the picked-up one in order to quantify the electric conductivity of the rod.
  If the electric conductivity differs from the reference value, consider the rod for checking or recycling. This reference value can be calculated or found in calibration phases, previous or periodical.

BRIEF DESCRIPTION OF THE SEVERAL VIEWS OF THE DRAWINGS

For a better understanding of the invention the following figures are included:

FIG. 1: schematic representation of an embodiment of the device.

FIG. 2: example of reading of the magnetic field pickup device, showing the places with and without coating.

DETAILED DESCRIPTION OF THE INVENTION

In the following an embodiment of the invention is briefly described, as an illustrative and non-limitative example thereof.

The device of the invention comprises a variable magnetic field generator (1), which can be one or more coils, and a magnetic field pickup device (2), which generally will be another one or other coils. Alongside both devices will be located the fuel rod (3) with the pellets having the zirconium diboride coating intended to be measured. The pickup device (2) shall issue the received magnetic field to a control system (4), which shall make the comparison between the generated magnetic field and the picked-up one. Through subtraction of both signals it is possible to quantify the variation of the electric conductivity of the rod (3) due to the presence of pellets with a coating of $ZrB_2$ in some zones of the rod (3) under measurement.

Preferably, the control system (4) shall comprise a second generator (1'), identical to generator (1) and a second pickup device (2'), identical to pickup device (2), at an identical distance but remote from the rod (3) so as to not being affected by its effect. In this way, the effect of the rod (3) can be isolated, without having to refer to theoretical values of generated field. It is also possible to perform initially measurements in vacuum, without rod (3), in order to find the reference value of the generated field.

The most effective solution is to arrange centred coils in the rod (3) as a generator (1) and as a pickup device (2) and connected through a Wheatstone bridge. The control system (4) would be identical.

In order to perform the process continuously throughout the length of the rod (3), the device shall have a bar (3) supplier (5) thereof, with variable speed between 10 and 200 mm/s, generally 50 mm/s. The advancement speed depends on the configuration of the remaining checking or inspection operations in the scanner where the device is integrated.

Considering the difference in electric conductivity between pellets with $ZrB_2$ and without $ZrB_2$ when the rod (3) passes, a differential signal shall be observed which allows identifying where begins and where ends the zone with pellets with IFBA (FIG. 2). If the value of conductivity is also analysed, if the coating is enough or if the rod (3) must be removed for a more deep examination, can be checked.

The method for checking the fuel rod comprises therefore the steps of:
  Arranging the rod (3) to be measured between the generator (1) and the pickup device (2).
  Generation of a variable magnetic field in the generator (1).
  Picking-up of the magnetic field.
  Comparison between the generated magnetic field and the picked-up one in order to quantify the electric conductivity of the rod (3)
  If the electric conductivity differs from the expected reference value, consider the rod (3) for checking, recycling, or the corresponding procedure for non-compliant rods (3).

Preferably all these steps shall be performed continuously, through the aforesaid bar (3) supplier (5).

The reference value can be calculated or found out in a previous calibration phase, introducing rods (3) whose coating is known. This calibration can be repeated periodically in order to check the reference value.

The magnetic field shall be typically created in a coil with low frequency (between 1 and 30 kHz, generally, although it can reach 100 kHz or more), with an excitation voltage of a few volts (2-15 V). However, both frequency and voltage shall depend on the characteristics of the generator (1) and of the pickup device (2).

The frequency of the magnetic field shall depend also of external factors. For example, if the pellets are within a metal sheath (for example, circaloy), which is currently the standard, the sheath makes a screening when the frequency is very high (in the order of megahertz or higher). If the sheath is made of other material, such as composites or ceramics, this phenomenon does not occur and those frequencies can be used.

In FIG. 2 can be seen an example of the application of the final reading for a dummy rod, composed of a circaloy tube, of 9.5 mm in outer diameter, 8.4 mm in inner diameter, packed with alumina pellets coated with $ZrB_2$ (6) and alumina pellets (7) (non-conductive). The vertical axis is intensity, in decibels, whereas the horizontal one can be distance or time, because these area directly connected by the known steady speed.

We claim:

1. Device for checking fuel rods with IFBA (Integral Fuel Burnable Absorber), their zirconium diboride coating, characterised in that it comprises a first variable magnetic field generator and a first magnetic field pickup device, arranged in the vicinity of the rod, as well as a control system for comparing a generated variable magnetic field and a picked-up magnetic field.

2. Device according to claim 1, further comprising a bar supplier.

3. Device according to claim 2, wherein the bar supplier circulates the rod at a speed between 10 and 200 mm/s.

4. Device according to claim 3, wherein the speed is 50 mm/s.

5. Device according to claim 1, wherein the first variable magnetic field generator is one or more coils.

6. Device according to claim 1, wherein the first magnetic field pickup device is one or more coils.

7. Device according to claim 1, wherein the control system is composed of a second variable magnetic field generator and a second magnetic field pickup device, identical to generator and pickup device tz1 respectively and arranged in the same relative position, and isolated from the rod.

8. Method for checking fuel rods with IFBA, with the device of claim 1, comprising the steps of:
  arranging the rod to be measured between the variable magnetic field generator and the magnetic field pickup device;
  generation of the variable magnetic field in the generator;
  picking-up of the magnetic field;
  comparison between the generated variable magnetic field and the picked-up magnetic field in order to quantify electric conductivity of the rod;
  if the electric conductivity differs from a reference value, consider the rod for checking or recycling.

9. Method according to claim 8, wherein the steps are performed continuously by a bar supplier.

10. Method according to claim 8, wherein the reference value is in a previous calibration phase.

11. Method according to claim 10, wherein the reference value is checked periodically.

12. Method according to claim 8, wherein the picked-up magnetic field is compared to a magnetic field produced in a control system composed of a second variable magnetic field generator and a second magnetic field pickup device, identical to the first variable magnetic field generator and the first magnetic field pickup device respectively and arranged in the same relative position, and isolated from the rod.

* * * * *